(12) United States Patent
Gu et al.

(10) Patent No.: US 12,110,998 B2
(45) Date of Patent: Oct. 8, 2024

(54) PIPE FITTING CONNECTOR

(71) Applicant: WUXI JINHUA YIYUAN TECHNOLOGY CO., LTD, Wuxi (CN)

(72) Inventors: Niandong Gu, Wuxi (CN); Xiaojia Lu, Wuxi (CN)

(73) Assignee: WUXI JINHUA YIYUAN TECHNOLOGY CO., LTD, Wuxi (CN)

( * ) Notice: Subject to any disclaimer, the term of this patent is extended or adjusted under 35 U.S.C. 154(b) by 25 days.

(21) Appl. No.: 18/098,265

(22) Filed: Jan. 18, 2023

(65) Prior Publication Data
US 2023/0151917 A1 May 18, 2023

Related U.S. Application Data

(63) Continuation of application No. PCT/CN2022/124645, filed on Oct. 11, 2022.

(51) Int. Cl.
*F16L 37/098* (2006.01)

(52) U.S. Cl.
CPC .................. *F16L 37/098* (2013.01)

(58) Field of Classification Search
CPC ... F16L 37/098; F16L 37/0847; F16L 37/096; F16L 37/12; F16L 37/1205; F16L 37/127; F16L 37/133; F16L 37/138
See application file for complete search history.

(56) References Cited

U.S. PATENT DOCUMENTS

| 2007/0007761 | A1 | 1/2007 | Nisel |
| 2009/0200796 | A1* | 8/2009 | Lai .......................... F16L 37/32 285/317 |
| 2018/0299047 | A1 | 10/2018 | Picton |
| 2018/0331517 | A1 | 11/2018 | Parker |
| 2019/0024834 | A1* | 1/2019 | Mao ..................... F16L 37/0985 |

* cited by examiner

*Primary Examiner* — Aaron M Dunwoody
(74) *Attorney, Agent, or Firm* — Hemisphere Law, PLLC; Zhigang Ma

(57) ABSTRACT

The present disclosure relates to the technical field of pipe fittings, specifically a pipe fitting connector. The pipe fitting connector includes a first connection member and a second connection member; the first connection member includes a first columnar pipe fitting, and a sealing member arranged on an outer wall of the first connection member; the second connection member includes a second columnar pipe fitting and a locking piece; the first columnar pipe fitting extends into the second columnar pipe fitting; the sealing member is located between an outer wall of the first columnar pipe fitting and an inner wall of the second columnar pipe fitting to seal the first connection member to the second connection member; and the locking piece is used for locking the first connection member to the second connection member.

14 Claims, 2 Drawing Sheets

PIPE FITTING CONNECTOR

TECHNICAL FIELD

The present disclosure relates to the technical field of pipe fittings, and specifically relates to a pipe fitting connector.

BACKGROUND

A pipe fitting connector is a device used to realize quick connection and quick disconnection between pipe fittings, and has been widely used in various industries. For example, the pipe fitting connector is generally applied to washing machines, refrigerators and the like in the household appliance industry. It can hermetically connect two sections of a pipe fitting to make water flow. The pipe fitting connector is also used in other fields. For example, different sets of equipment usually need to be connected in the medical industry to communicate two sets of equipment to introduce air or feed liquid. However, it is difficult to unify the sizes of various equipment pipe fittings, so a pipe fitting connector is often required.

The existing pipe fitting connector generally realizes connection by fasteners and is sealed by means of rubber or silica gel, so that the existing pipe fitting connector features with good sealing performance and quick connection and disconnection. However, it also has defects: The rubber or silica gel seals inner and outer surfaces of pipe fittings at both ends by its own elasticity and locks the pipe fittings through fastener structures. However, the fastener structures of the existing pipe fitting connector can hardly achieve a long-lasting sealing effect. That is, the pipe fitting connector needs to be replaced frequently, which leads to an increase in the use cost. Therefore, breaking through the sealing persistence of the pipe fitting connector is a subject that needs to be emphatically studied in the field.

Based on the above defects, the present disclosure discloses a pipe fitting connector, which is used for solving the defects in the prior art.

SUMMARY

The present disclosure aims to provide a pipe fitting connector to solve the problems mentioned in the background section.

In order to solve the above technical problems, the present disclosure provides the following technical solution. A pipe fitting connector includes a first connection member and a second connection member. The first connection member includes a first columnar pipe fitting, and a sealing member arranged on an outer wall of the first connection member; the second connection member includes a second columnar pipe fitting and a locking piece; the first columnar pipe fitting extends into the second columnar pipe fitting; the sealing member is located between an outer wall of the first columnar pipe fitting and an inner wall of the second columnar pipe fitting to seal the first columnar pipe fitting to the second columnar pipe fitting; the locking piece is connected to the first connection member; the locking piece includes elastic arms and hooks; when the first connection member is sealed to the second connection member, the elastic arms extend into locking through holes formed in the second connection member to generate a pre-tightening force on inner walls of the locking through holes; and the hooks are simultaneously hooked to end faces of the locking through holes to lock the first connection member to the second connection member.

Preferably, the locking piece includes an annular member sleeving the first connection member; the first connection member includes a first retainer and second retainers; the annular member is located between the first retainer and the second retainers, and is spaced apart from the first retainer and the second retainers by axial spaces.

Preferably, the first retainer is an annular bulge integrated with the first connection member; and the second retainers are several curved bulges arranged in a circumferential direction of the first connection member and integrated with the first connection member.

Preferably, two or more elastic arms are provided; the annular member, the elastic arms and the hooks are integrally formed, and the elastic arms and the annular member form a trapezoid structure.

Preferably, one side of each elastic arm away from the first columnar pipe fitting is provided with antiskid lines.

Preferably, the second connection member includes two or more wall pieces; the wall pieces are located outside the second columnar pipe fitting, and the locking through holes are formed between the wall pieces and an outer wall of the second columnar pipe fitting; and a wall thickness of one side of each wall piece close to the first connection member is greater than a wall thickness of one side away from the first connection member.

Preferably, one end of the second columnar pipe fitting close to the first columnar pipe fitting is provided with an annular chamfer; one end of the annular chamfer extends to be connected to an end face of the second columnar pipe fitting, and the other end extends to be connected to the inner wall of the second columnar pipe fitting.

Preferably, the first connection member includes ring slots; the ring slots are formed on the outer wall of the first columnar pipe fitting; and the sealing member is arranged in the ring slots.

Preferably, the first connection member further includes an edge slot; the edge slot is formed in an outer edge of an end portion of the first columnar pipe fitting; the second connection member further includes a flange; the flange is located in the middle of the inner wall of the second columnar pipe fitting; and the flange and the edge slot match each other when the first columnar pipe fitting is placed in the second columnar pipe fitting.

Compared with the prior art, the present disclosure achieves the following beneficial effects:

First, the pre-tightening force generated by deformation of the elastic arms of the pipe fitting connector disclosed by the present disclosure will continuously generate a pre-tightening action on the inner walls of the locking through holes on the second connection member, so that a long-lasting sealing effect is guaranteed between the first connection member and the second connection member, and the defect that it is hard for the traditional connector to constantly keep the sealing performance.

Second, according to the pipe fitting connector disclosed by the present disclosure, axial movement and circumferential rotation cannot occur between the first connection member and the second connection member because of the hooks, which further achieves locking between the first connection member and the second connection member, improves the anti-separation force and prevents the locking piece from falling off.

Then, according to the pipe fitting connector disclosed by the present disclosure, when the hooks are hooked to the locking through holes, the annular member will slightly axially move relative to the first connection member, so that the annular member abuts against the end face of the first retainer. By means of the action of transfer forces of the elastic arms, the hooking action of the hooks to the end faces of the locking through holes is completed. In this way, the matching precision for the hooks and the locking through holes can be reduced, which facilitates the production; and the locking piece is hard to break due to the elasticity.

Finally, according to the pipe fitting connector disclosed by the present disclosure, the annular chamfer can facilitate the sealing member to enter and leave the second columnar pipe fitting.

BRIEF DESCRIPTION OF THE DRAWINGS

The accompanying drawings are used to provide a further understanding of the present disclosure and constitute a part of this specification to explain the present disclosure together with the embodiments of the present disclosure, and do not constitute restrictions to the present disclosure. In the drawings.

Figure 1:
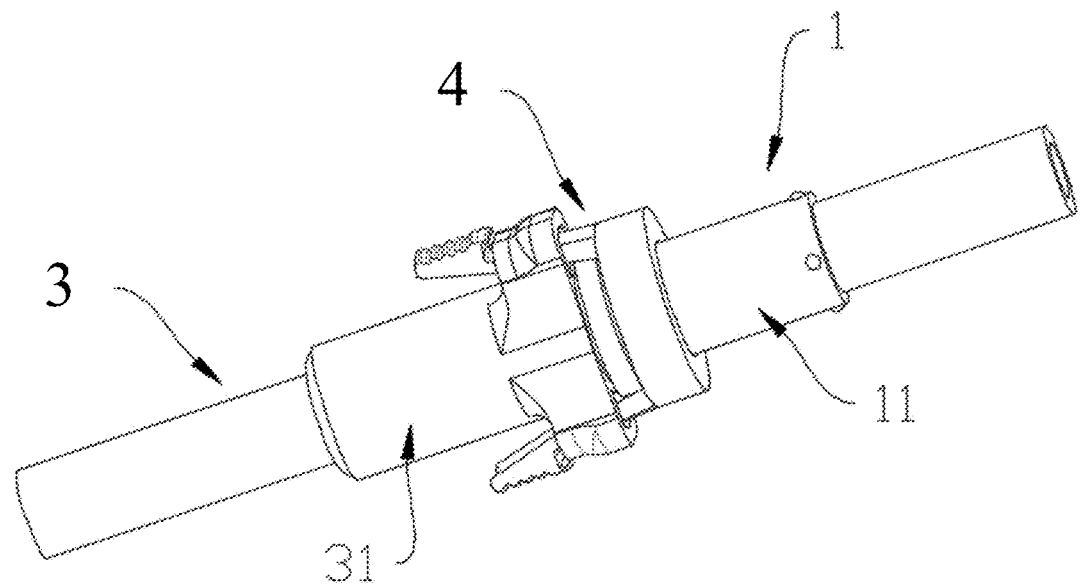
FIG. 1 is a schematic three-dimensional diagram of a pipe fitting connector in an embodiment of the present disclosure.

In the drawings:
- first connection member 1, first columnar pipe fitting 11, first retainer 12, second retainer 13, ring slot 14, and edge slot 15;
- sealing member 2;
- second connection member 3, second columnar pipe fitting 31, locking through hole 32, wall piece 33, annular chamfer 34, and flange 35;
- locking piece 4, elastic arm 41, hook 42, annular member 43, and antiskid line 44.

DETAILED DESCRIPTION OF THE EMBODIMENTS

The technical solutions in the embodiments of the present disclosure will be described clearly and completely below with reference to the drawings in the embodiments of the present disclosure. Obviously, the embodiments described herein are only part of the embodiments of the present disclosure, not all the embodiments. Based on the embodiments in the present disclosure, all other embodiments obtained by those of ordinary skill in the art without creative work shall fall within the protection scope of the present disclosure.

The existing pipe fitting connector generally realizes connection by fasteners and is sealed by means of rubber or silica gel, so that the existing pipe fitting connector features with good sealing performance and quick connection and disconnection. However, it also has defects: The rubber or silica gel seals inner and outer surfaces of pipe fittings at both ends by its own elasticity and locks the pipe fittings through fastener structures. However, the fastener structures of the existing pipe fitting connector can hardly achieve a long-lasting sealing effect. That is, the pipe fitting connector needs to be replaced frequently, which leads to an increase in the use cost.

Based on the above defects, the present disclosure provides an embodiment of a pipe fitting connector as an optimal implementation of the pipe fitting connector to solve the problems in the prior art.

Figure 2:
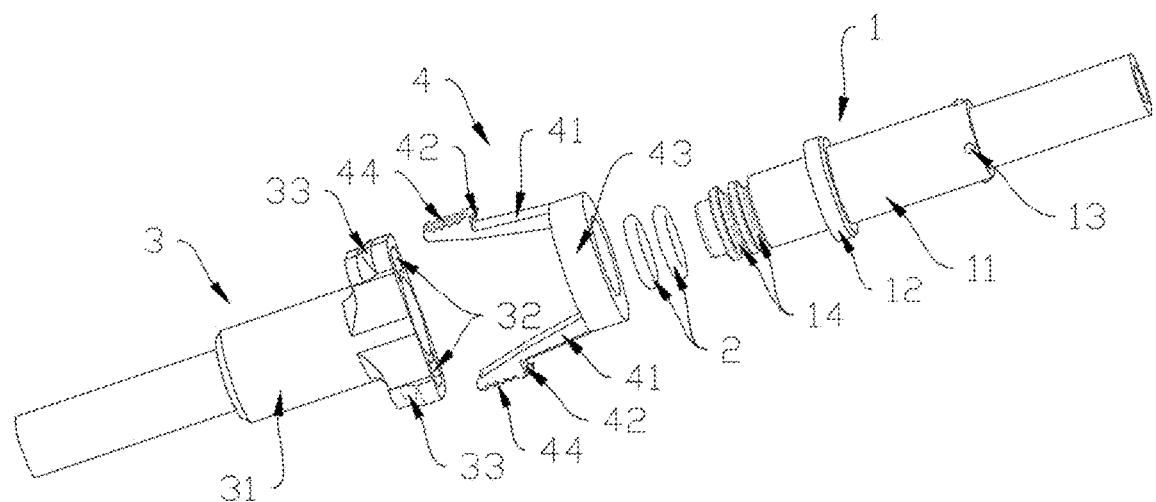
FIG. 2 is an exploded diagram of a pipe fitting connector in an embodiment of the present disclosure.

Specifically, as shown in FIG. 1 to FIG. 2, the pipe fitting connector includes a first connection member 1. The first connection member 1 includes a first columnar pipe fitting 11 used for transporting fluid, and further includes a sealing member 2. The sealing member 2 is arranged on an outer wall of the first connection member 1, and is preferably an annular rubber ring sleeving the first connection member 1 to achieve a sealing effect. The pipe fitting connector further includes a second connection member 3. The second connection member 3 includes a second columnar pipe fitting 31 used for being hermetically connected to the first connection member 1. Hermetical connection between a first pipe fitting and a second pipe fitting can be achieved when the first columnar pipe fitting 11 and the second columnar pipe fitting 31 are hermetically connected to each other.

Specifically, a connection way for the first columnar pipe fitting 11 and the second columnar pipe fitting 31 is as follows: As shown in FIG. 1 to FIG. 2, the first columnar pipe fitting 11 extends into the second columnar pipe fitting 31, so that the sealing member 2 is located between an outer wall of the first columnar pipe fitting 11 and an inner wall of the second columnar pipe fitting 31 to seal the first connection member 1 to the second connection member 3, thus achieving the hermetical connection between the first pipe fitting and the second pipe fitting.

Further, long-lasting connection between the first connection member and the second connection member cannot be achieved until a locking force is provided for the connection between the first columnar pipe fitting 11 and the second columnar pipe fitting 31. Based on this, as shown in FIG. 1 to FIG. 2, this connector further includes a locking piece 4. The locking piece 4 is connected to the first connection member 1. The locking piece 4 includes elastic arms 41 and hooks 42. When the first connection member 1 and the second connection member 3 are hermetically connected, the elastic arms 41 extend into locking through holes 32 formed in the second connection member 3 to generate a pre-tightening force on inner walls of the locking through holes 32. The hooks 42 are hooked to end faces of the locking through holes 32 to lock the first connection member 1 to the second connection member 3. The pre-tightening force generated by the elastic arms 41 on the inner walls of the locking through holes 32 will lock the connection between the first connection member 1 and the second connection member 3 to prevent the looseness between them. Meanwhile, the pre-tightening force generated by the deformation of the elastic arms 41 will continuously act on the inner walls of the locking through holes 32, so as to guarantee a long-lasting sealing effect between the first connection member 1 and the second connection member 3, which overcomes the defects of the traditional connector. In addition, axial movement and circumferential rotation cannot occur between the first connection member 1 and the second connection member 3 because of the hooks 42, which further achieves locking between the first connection member and the second connection member, improves the anti-separation force and prevents the locking piece 4 from falling off.

Further, in another embodiment of the connector, a connection way for the locking piece 4 and the first connection member 1 is specifically as follows: As shown in FIG. 1 to FIG. 2, the locking piece 4 includes an annular member 43 sleeving the first connection member 1. The first connection member 1 includes a first retainer 12 and second retainers 13. The annular member 43 is located between the first retainer 12 and the second retainers 13, and is spaced apart from the first retainer 12 and the second retainers 13 by axial spaces. Due to the spaces, there is a certain loosening degree between the locking piece 4 and the first connection member 1. When the hooks 42 are hooked to locking through holes, the annular member 43 will slightly axially move relative to the first connection member 1, so that the annular member 43 abuts against the end face of the first retainer 12. By means of the action of transfer forces of the elastic arms 41, the hooking action of the hooks 42 to the end faces of the locking through holes 32 is completed. In this way, the matching precision for the hooks 42 and the locking through holes can be reduced, which facilitates the production; and the locking piece 4 is hard to break due to the elasticity.

Further, as shown in FIG. 2, in order to facilitate the assembling of the locking piece 4, in another embodiment of the connector, the first retainer 12 is an annular bulge integrated with the first connection member 1. The second retainers 13 are several curved bulges arranged in a circumferential direction of the first connection member 1 and integrated with the first connection member 1. The curved bulges facilitate the assembling between the locking piece 4 and the first connection member 1. After the first pipe fitting is fixedly connected to the first connection member 1, the locking piece 4 can sleeve the first pipe fitting from the other end of the first pipe fitting. The annular member 43 can across the curved bulges under the condition of applying an acting force and is placed between the first retainer 12 and the second retainers 13. The curved shapes of the curved bulges are convenient for the annular member 43 to across.

Further, as shown in FIG. 2, in another embodiment of the connector, in order to provide a multidirectional and uniform pre-tightening force to the second connection member 3, there are two or more elastic arms 41. In this embodiment, there are preferably two elastic arms 41. Correspondingly, there are also two locking through holes 32. The annular member 43, the elastic arms 41 and the hooks 42 are integrally formed and are prepared from plastic, so that the elastic arms 41 can deform to generate an elastic force.

Further, as shown in FIG. 2, in another embodiment of the connector, the elastic arms 41 and the annular member 43 form a trapezoid structure. In this way, in a free state, the elastic arms 41 cannot directly correspond to the locking through holes 32. When entering the locking through holes 32, the elastic arms 41 deform under the action of the inner walls of the locking through holes 32, and then generate the pre-tightening force. In this embodiment, a field angle of the trapezoid structure is 10°.

Further, as shown in FIG. 2, in another embodiment of the connector, one side of each elastic arm 41 away from the first columnar pipe fitting 11 is provided with antiskid lines 44. The antiskid lines 44 are specifically composed of several antiskid slots for facilitating manual handling.

Further, as shown in FIG. 2, in another embodiment of the connector, the locking through holes 32 are specifically as follows: The second connection member 3 includes two or more wall pieces 33. The wall pieces 33 are located outside the second columnar pipe fitting 31, and the locking through holes 32 are formed between the wall pieces and an outer wall of the second columnar pipe fitting 31. A wall thickness of one side of each wall piece 33 close to the first connection member 1 is greater than a wall thickness of one side away from the first connection member 1. In this way, the resistance of the locking through holes 32 to the hooks 42 is increased, and deformation of the wall pieces 33 is prevented.

Figure 4:
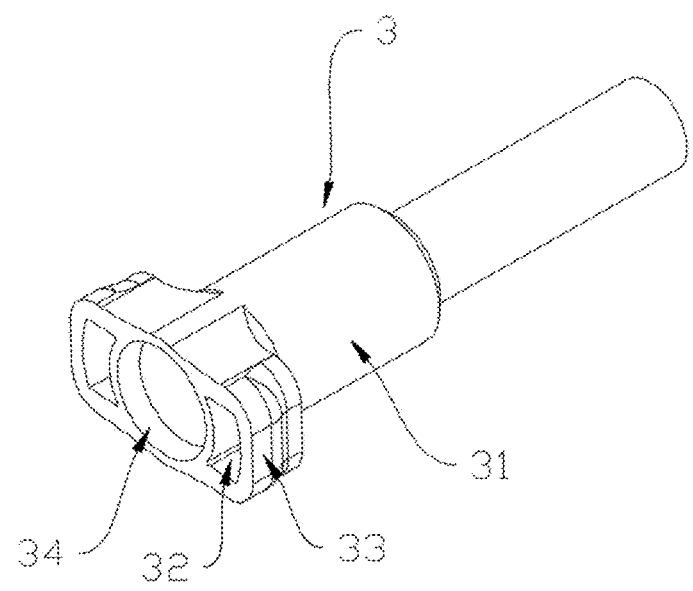
FIG. 4 is a three-dimensional diagram of a second connection member in an embodiment of the present disclosure.

Further, as shown in FIG. 4, in another embodiment of the connector, one end of the second columnar pipe fitting 31 close to the first columnar pipe fitting 11 is provided with an annular chamfer 34. One end of the annular chamfer 34 extends to be connected to an end face of the second columnar pipe fitting 31, and the other end extends to be connected to the inner wall of the second columnar pipe fitting 31. The annular chamber 34 can facilitate the sealing member 2 to enter and leave the second columnar pipe fitting 31.

Further, as shown in FIG. 2, in order to prevent the sealing member 2 from falling off in the assembling process, in another embodiment of the connector, the first connection member 1 includes ring slots 14. The ring slots 14 are formed on the outer wall of the first columnar pipe fitting 11. The sealing member 2 is arranged in the ring slots 14.

Figure 3:
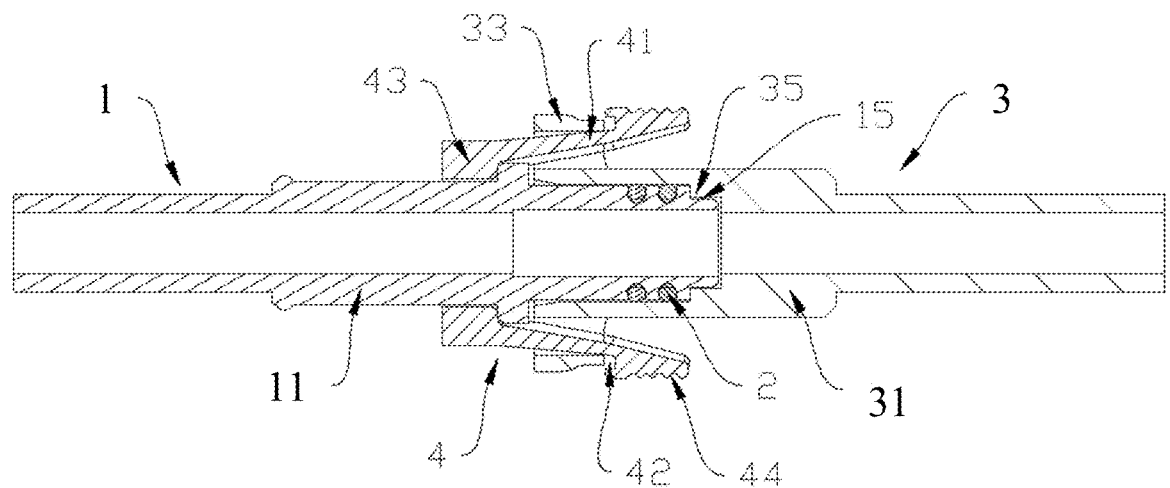
FIG. 3 is a sectional view of an unconnected pipe fitting connector in an embodiment of the present disclosure.

Further, in another embodiment of the connector, in order to prevent the first connection member 1 and the second connection member 3 from axially moving after the hermetical connection, as shown in FIG. 3, the first connection member 1 further includes an edge slot 15. The edge slot 15 is formed in an outer edge of an end portion of the first columnar pipe fitting 11. The second connection member 3 further includes a flange 35. The flange 35 is located in the middle of the inner wall of the second columnar pipe fitting 31. The flange 35 and the edge slot 15 match each other when the first columnar pipe fitting 11 is placed in the second columnar pipe fitting 31, which can guarantee axial fixing between the first connection member 1 and the second connection member 3.

It should be noted that in this context, relational terms such as first and second are used merely to distinguish one entity or operation from another entity or operation, instead of necessarily requiring or implying that these entities or operations have any of these actual relationships or orders. Furthermore, terms "include", "including" or any other variants are meant to cover non-exclusive inclusions, so that a process, method, object or device that includes a series of elements not only includes those elements, but also includes other elements which are not definitely listed, or further includes inherent elements of this process, method, object or device.

It should be finally noted that the above descriptions are only preferred embodiments of the present disclosure and are not intended to limit the present disclosure. Although the present disclosure has been described in detail with reference to the foregoing embodiments, those skilled in the art can still modify the technical solutions in the foregoing various embodiments, or equivalently replace partial technical features. Any modifications, equivalent replacements, improvements and the like that are made without departing from the spirit and principle of the present disclosure shall fall within the protection scope of the present disclosure.

What is claimed is:

1. A pipe fitting connector, comprising:
   a first connection member (1), wherein the first connection member (1) comprises a first columnar pipe fitting (11);
   a sealing member (2), wherein the sealing member (2) is arranged on an outer wall of the first connection member (1);
   a second connection member (3), wherein the second connection member (3) comprises a second columnar pipe fitting (31); the first columnar pipe fitting (11) extends into the second columnar pipe fitting (31); the sealing member (2) is located between an outer wall of the first columnar pipe fitting (11) and an inner wall of the second columnar pipe fitting (31) to seal the first connection member (1) to the second connection member (3);

and a locking piece (4), wherein the locking piece (4) is connected to the first connection member (1); the locking piece (4) comprises an annular member (43), two or more elastic arms (41) and hooks (42); wherein the annular member (43) is sleeved on the first connection member (1); the annular member (43), the elastic arms (41) and the hooks (42) are integrally formed; wherein the elastic arms (41) extend from the annular member (43), and the elastic arms (41) and the annular member (43) form a trapezoid structure; the hook (42) is formed on an outside surface of one end of the elastic arms (41) away form the annular member (43); when the first connection member (1) and the second connection member (3) are sealed, the elastic arms (41) extend into locking through holes (32) formed in the second connection member (3) to generate a pre-tightening force on inner walls of the locking through holes (32); and the hooks (42) are simultaneously hooked to end faces of the locking through holes (32) to lock the first connection member (1) to the second connection member (3).

2. The pipe fitting connector according to claim 1, wherein
the first connection member (1) comprises a first retainer (12) and second retainers (13); the annular member (43) is located between the first retainer (12) and the second retainers (13), and is spaced apart from the first retainer (12) and the second retainers (13) by axial spaces.

3. The pipe fitting connector according to claim 2, wherein
the first retainer (12) is an annular bulge integrated with the first connection member (1);
the second retainers (13) are several curved bulges arranged in a circumferential direction of the first connection member (1) and integrated with the first connection member (1).

4. The pipe fitting connector according to claim 1, wherein one side of each elastic arm (41) away from the first columnar pipe fitting (11) is provided with antiskid lines (44).

5. The pipe fitting connector according to claim 1, wherein
the second connection member (3) comprises two or more wall pieces (33); the wall pieces (33) are located outside the second columnar pipe fitting (31), and the locking through holes (32) are formed between the wall pieces and an outer wall of the second columnar pipe fitting (31); and a wall thickness of one side of each wall piece (33) close to the first connection member (1) is greater than a wall thickness of one side away from the first connection member (1).

6. The pipe fitting connector according to claim 1, wherein one end of the second columnar pipe fitting (31) close to the first columnar pipe fitting (11) is provided with an annular chamfer (34); one end of the annular chamfer (34) extends to be connected to an end face of the second columnar pipe fitting (31), and the other end of the annular chamfer (34) extends to be connected to the inner wall of the second columnar pipe fitting (31).

7. The pipe fitting connector according to claim 1, wherein the first connection member (1) comprises ring slots (14); the ring slots (14) are formed on the outer wall of the first columnar pipe fitting (11); and the sealing member (2) is arranged in the ring slots (14).

8. The pipe fitting connector according to claim 1, wherein
the first connection member (1) further comprises an edge slot (15); the edge slot (15) is formed in an outer edge of an end portion of the first columnar pipe fitting (11);
the second connection member (3) further comprises a flange (35); the flange (35) is located in the middle of the inner wall of the second columnar pipe fitting (31); and
the flange (35) and the edge slot (15) match each other when the first columnar pipe fitting (11) is placed in the second columnar pipe fitting (31).

9. A pipe fitting connector, comprising:
a first connection member (1), wherein the first connection member (1) comprises a first columnar pipe fitting (11), a first retainer (12) and second retainers (13); wherein the first retainer (12) is an annular bulge integrated with the first connection member (1); the second retainers (13) are several curved bulges arranged in a circumferential direction of the first connection member (1) and integrated with the first connection member (1);
a sealing member (2), wherein the sealing member (2) is arranged on an outer wall of the first connection member (1);
a second connection member (3), wherein the second connection member (3) comprises a second columnar pipe fitting (31); the first columnar pipe fitting (11) extends into the second columnar pipe fitting (31); the sealing member (2) is located between an outer wall of the first columnar pipe fitting (11) and an inner wall of the second columnar pipe fitting (31) to seal the first connection member (1) to the second connection member (3);
and a locking piece (4), wherein the locking piece (4) is connected to the first connection member (1); the locking piece (4) comprises an annular member (43), elastic arms (41) and hooks (42); wherein the annular member (43) is sleeved on the first connection member (1), located between the first retainer (12) and the second retainers (13), and spaced apart from the first retainer (12) and the second retainers (13) by axial spaces; the elastic arms (41) extend from the annular member (43); the hook (42) is formed on an outside surface of one end of the elastic arms (41) away form the annular member (43); when the first connection member (1) and the second connection member (3) are sealed, the elastic arms (41) extend into locking through holes (32) formed in the second connection member (3) to generate a pre-tightening force on inner walls of the locking through holes (32); and the hooks (42) are simultaneously hooked to end faces of the locking through holes (32) to lock the first connection member (1) to the second connection member (3).

10. The pipe fitting connector according to claim 9, wherein one side of each elastic arm (41) away from the first columnar pipe fitting (11) is provided with antiskid lines (44).

11. The pipe fitting connector according to claim 9, wherein
the second connection member (3) comprises two or more wall pieces (33); the wall pieces (33) are located outside the second columnar pipe fitting (31), and the locking through holes (32) are formed between the wall pieces and an outer wall of the second columnar pipe fitting (31); and a wall thickness of one side of each wall piece (33) close to the first connection member (1) is greater than a wall thickness of one side away from the first connection member (1).

12. The pipe fitting connector according to claim 9, wherein one end of the second columnar pipe fitting (31) close to the first columnar pipe fitting (11) is provided with an annular chamfer (34); one end of the annular chamfer (34) extends to be connected to an end face of the second columnar pipe fitting (31), and the other end of the annular chamfer (34) extends to be connected to the inner wall of the second columnar pipe fitting (31).

13. The pipe fitting connector according to claim 9, wherein the first connection member (1) comprises ring slots (14); the ring slots (14) are formed on the outer wall of the first columnar pipe fitting (11); and the sealing member (2) is arranged in the ring slots (14).

14. The pipe fitting connector according to claim 9, wherein
- the first connection member (1) further comprises an edge slot (15); the edge slot (15) is formed in an outer edge of an end portion of the first columnar pipe fitting (11);
- the second connection member (3) further comprises a flange (35); the flange (35) is located in the middle of the inner wall of the second columnar pipe fitting (31); and
- the flange (35) and the edge slot (15) match each other when the first columnar pipe fitting (11) is placed in the second columnar pipe fitting (31).

* * * * *